Figure 1:
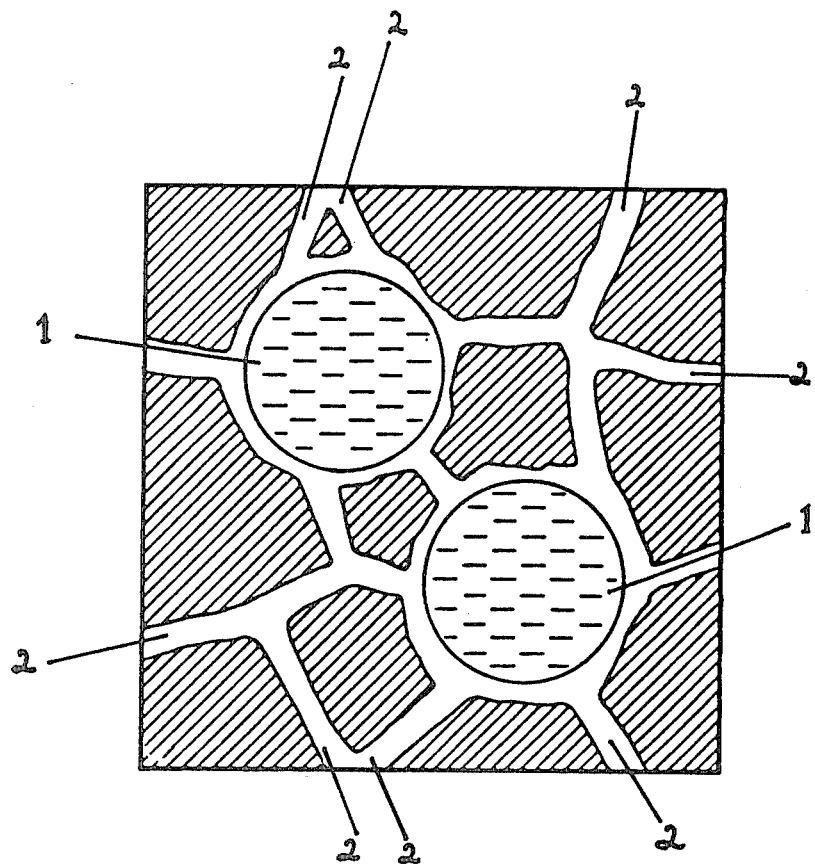

United States Patent [19]

Villadsen et al.

[11] 4,224,190
[45] Sep. 23, 1980

[54] CATALYST FOR DEHYDROGENATING ORGANIC COMPOUNDS, IN PARTICULAR AMINES, THIOLS, AND ALCOHOLS, AND A PROCESS FOR ITS PREPARATION

[76] Inventors: John Villadsen; Hans Livbjerg; Carl E. Moller, all of Bygning 229, 2800 Lyngby, Denmark

[21] Appl. No.: 925,930

[22] Filed: Jul. 19, 1978

[30] Foreign Application Priority Data

Jul. 22, 1977 [DK] Denmark .............................. 3315/77

[51] Int. Cl.² ........................ B01J 23/08; B01J 23/06
[52] U.S. Cl. .................................... 252/463; 252/475
[58] Field of Search ...................... 252/463, 475, 447

[56] References Cited

U.S. PATENT DOCUMENTS

| | | | |
|---|---|---|---|
| 3,254,055 | 5/1966 | Smith | 252/463 X |
| 3,338,972 | 8/1967 | Young | 252/475 X |
| 3,523,964 | 8/1970 | Kober et al. | 252/475 X |

*Primary Examiner*—Carl F. Dees

[57] ABSTRACT

Alcohols are dehydrogenated to form ketones, using a catalyst containing liquid indium dispersed and retained in the pore structure of a porous carrier. The catalyst is prepared by mixing powdered $In_2O_3$ and MgO, firing the mixture at 900°–1150° C. for 5–20 hours, and activating the catalyst by passing through a reducing gas.

7 Claims, 2 Drawing Figures

CATALYST FOR DEHYDROGENATING ORGANIC COMPOUNDS, IN PARTICULAR AMINES, THIOLS, AND ALCOHOLS, AND A PROCESS FOR ITS PREPARATION

The present invention relates to a catalyst for dehydrogenating organic compounds, in particular amines, thiols, and alcohols.

Mr. E. W. R. Steacie and Mr. E. L. Elkin, Pros. Roy. Soc. A. 142 457 (1933) were the first to describe dehydrogenation of organic compounds by means of fused metals as a catalytic material, whereby it was proved that zinc may catalyze the conversion of methanol into formaldehyde and hydrogen with an activity showing no abrupt change (break) at the melting point of Zn (419° C.). This observation was unexpected and surprising since it was contrary to the prevailing theory that the catalytic activity of metals is mainly attributable to the so-called active spots located about crystal boundaries and dislocations in the crystal lattice. Such active spots cannot, of course, appear on the surface of fused metal.

Mr. C. M. Schwab, Dechema Monographien 38, 205 (1960) has examined the catalytic effect of fused Sn, Tl and Hg on the dehydrogenation of formic acid to obtain $CO_2$ and $H_2$. This work stresses the great advantages obtainable if well dispersed, fused metals could be used as a catalyst for dehydrogenating reactions instead of solid, porous catalysts. Thus the typical heterogeneous catalysts are characterized by the active material, e.g. a metal, being finely dispersed as crystallites in the porous, inactive carrier material, and by the active spots of the active material being susceptible to poisoning, e.g. due to the deposit of cracking products on the spots. On the contrary, a surface of fused metal cannot be poisoned in consequence of the continuous renewal of the surface until the complete amount of catalytic material has been poisoned. The proposal described in the above publication for dispersing fused catalytic metals by an atomization process is, however, quite impracticable, and since a large metal surface is necessary for obtaining a large contact area between the reactant and the metal in order to obtain a satisfactory utilization of the catalyst, said proposal has hardly become of any practical importance.

Mr. Y. Saito, Mr. N. Hiramasu, Mr. N. Kawanami and Mr. Y. Ogino, Bull. Jap. Petr. Inst. 14, 169 (1972), have been working with dehydrogenation of a large number of alcohols by means of Zn, In, and Ga, and Mr. K. Okavo, Mr. Y. Saito and Mr. Y. Ogino, Bull. Chem. Soc. Japan, 45, 69 (1972), have correspondingly been working with dehydrogenation of amines by means of the same liquid metals. In both cases the contact area between the gas phase and the metal is provided either by bubbling the gas through the liquid metal or by passing the gas across a reservoir of the fused metal. In both cases a very limited contact area is obtained, but by means of the catalysts used in such manner it was in principle found possible to dehydrogenate aliphatic and aromatic alcohols, which may be saturated or unsaturated, but which are either primary or secondary, while tertiary alcohols cannot be hydrogenated. Correspondingly, it was possible to dehydrogenate primary amines to form a nitrile or optionally a secondary, symmetrical amine, whereas secondary amines resulted in azomethines:

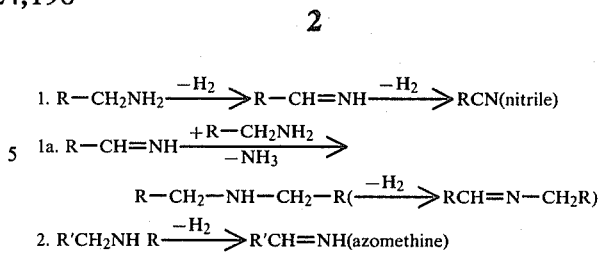

Thiols can be dehydrogenated as easily as alcohols, but instead of the unstable thion compounds ($>C=S$), dithio compounds are formed $$2 RSH \rightarrow RSSR + H_2,$$

for which reason both primary, secondary and tertiary thiols can be dehydrogentated.

The catalyst according to the invention is characterized by comprising a porous carrier containing liquid indium and/or zinc as an active catalytic material at the working temperature of the catalyst, said catalytic material in the shape of drops substantially with a diameter of 0.3–2$\mu$ being dispersed and maintained in the pore structure of the carrier.

As a result a contact area per gram of fused metal is obtained, which is about 40,000 times as large as the contact area obtained by the catalysts described in the above Japanese publication, the catalyst according to the invention thereby achieving an activity many times greater than the activity of known catalysts. Thus it has been proved that the dehydrogenation of 2-butanol→2-butanon at 450° C. when using liquid indium can only result in a conversion of some few percent when the alcohol is passed across the surface or is bubbled through the liquid metal, whereas by using the catalyst according to the invention an almost complete conversion may be obtained when using a considerably smaller amount of indium and a temperature of about 100° C. lower (350° C.).

An embodiment of the described catalyst wherein the liquid metal is indium is characterized by the catalyst having a porosity of 0.2–0.7 $cm^3/cm^3$, a BET-surface area of 0.5–10 $m^2/g$, and an In-content of 0.05 to 10 g per 100 g of fired catalyst, preferably an In-content of 0.5–1.5 g per 100 g of fired catalyst.

A catalyst of the above characterized kind was found to give excellent dehydrogenation results, as it will appear from the following test results.

The invention furthermore relates to a process for preparing the described catalyst, said process being characterized by mixing powdered $In_2O_3$ and/or ZnO with an earth alkali metaloxide or hydroxide, preferably MgO or Mg(OH)$_2$, whereafter the resulting mixture or substance is fired for 5 to 20 hours at a temperature of 900°–1150° C. and subsequently activated by introduction of a reducing gas, e.g. the organic compound in question in the form of vapor at 320°–440° C., until 2 to 3 times the calculated stoichiometric amount of gas for complete reduction of $In_2O_3$ to In and/or ZnO to Zn has passed through the catalyst.

Consequently, when using as the reducing gas the organic compound to be dehydrogenated in gaseous form, dehydrogenation of the organic compound will commence when the amount of gas as indicated above has passed through the catalyst.

From the outset it could seem impossible to capture a fused metal on a ceramic carrier, since the contact angle metal carrier is more than 90°. The contact angle In-MgO is for instance 133° at the melting point (156° C.) of indium. Therefore, the metal usually sweats out or runs out of the carrier unless if is retained by means of great external pressure. The phenomenon is known from the mercury porosimetry, whereby continuously increasing pressure p is necessary for making Hg penetrate the pores having a decreasing radius r (superatmospheric pressure $p = (-2\gamma \cos \theta)/r$, whereby $\gamma$ is the surface tension, r is the pore radius and $\theta$ the contact angle). The process according to the invention solves this problem since the reduction of $In_2O_3$-particles and/or ZnO-particles which were embedded in the carrier material during the mixing results in a final carrier material structure, wherein In-drops and/or Zn-drops formed from $In_2O_3$-particles and/or ZnO-particles during volume contraction, are present in cavities mutually connected through the pores of the carrier. The pores permit free passage of the gas to the surfaces of the microscopic metal drops, a spontaneous gatherings or penetration of the metal, however, being impossible due to the difference in the size of the cavities and the pore diameter.

FIG. 1 of the drawing illustrates a fractured surface in a catalyst pill according to the invention, drawn from a scanning electron microscope photograph. FIG. 1 clearly shows how spherical metal droplets 1 of from 0.5 to 2.5$\mu$ in size are separated by a duct system 2 of far less diameter than the pores encasing the droplets 1.

U.S. Pat. No. 3,542,878 discloses a catalyst prepared by impregnating a porous carrier with an aqueous solution of a tin compound and subsequently drying the same or by precipitating Sn(OH)Cl, $xH_2O$ on the carrier, whereby the tin compound is reduced with hydrogen. At about 250° C. and a reaction pressure of 75 ata, this catalyst results in aldol condensation of carbonyl compounds, and the catalytic activity is imputed to fused, metallic tin.

Figure 2:
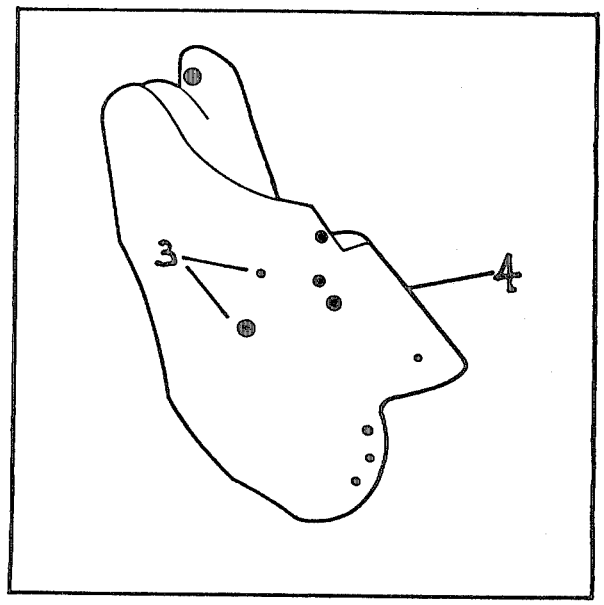

However, there is good reason to doubt whether water-soluble metal compounds or metal salts, which by impregnation and precipitation have been applied to a porous carrier, after reduction with hydrogen will result in a dispersion of fused metal in the carrier, said dispersion being stable at atmospheric pressures. As the result of testing the impregnation of a porous carrier with for instance an $In(NO_3)_3$-solution followed by drying and reduction of the indium salt, the metal ran off or was exuded from of the carrier, cf. the following Example 8 and FIG. 2 of the drawing. FIG. 2 illustrates such exuded spherical indinium droplets 3 of from 20 to 30$\mu$ in size on a quartz glass carrier particle 4 having a pore size of 306.0 nm. On the other hand precipitation of the carrier ($Mg(OH)_2$) around metaloxide granules ($In_2O_3$) as described in the following Example 9 or pelletizing of the powdered materials as described in the following Examples 1 to 7 results in the desired embedment of metal drops in cavities, from where they cannot escape.

The process of the invention provides a stable catalyst material, wherein a metal (indium and/or zinc) is dispersed. The catalytic properties of the catalyst on dehydrogenation reactions—in particular dehydrogenation of alcohols, amines, and thiols—are known per se, but which by virture of an extremely fine dispersion of the metal on the carrier material, it possesses an activity per unit of weight of metal, which is far greater than the activity of the metaloxide catalysts conventionally used for dehydrogenation reactions, and many thousand times larger than when the same metals are used in undispersed form, cf. the previously mentioned Japanese publications. The catalyst of the invention is quite different from the catalysts presently used within the industry for a number of dehydrogenation reactions, and by virtue of its high activity and selectivity it provides, as compared to known catalysts, a possibility of substantially increasing the reaction rate per unit of reactor volume and the product quality. In the following the use of the catalyst for dehydrogenating alcohols is described, and in particular the use of a catalyst based on indium for dehydrogenating 2-butanol is mentioned, but catalysts based on zinc are also described, the preparation of such being described in the following Example 10. Zinc is considerably less expensive than indium and would therefore be preferred to indium, if there were not at the same time some drawbacks that make zinc technically less suitable than indium. The catalytic effect of catalysts based on zinc has been proved, however.

2-butanon is an industrially important solvent, and 85% of the world market consumption is prepared by dehydrogenating 2-butanol. Among the used catalysts can be mentioned: copper-brass-chips or (rusty) iron filings, either alone or coated with a layer of one or more metaloxides such as ZnO, MgO, $Na_2O$, $Ce_2O_3$, $Cr_2O_3$, $ZrO_2$, $ThO_2$ and $Bi_2O_3$. When such a composite catalyst is used, it is due to the fact that the pure metal catalysts require a high temperature (475°–510° C. has been mentioned in U.S. Pat. No. 2,092,870) for obtaining an appropriately high conversion ratio (85%), but at such a high temperature the selectivity is poor, since part of the alcohol dehydrates, formation of butene and water taking place at the same time, and furthermore the quality of the ketone may be reduced due to the aldol condensation. U.S. Pat. No. 2,436,733 mentions that at 400° C. and F/W=1–1.5 per hour (F=the feed water rate in kilograms per hour and W=the amount of catalyst in kilograms) a conversion ratio of $\alpha = 93\%$ is achieved with a $ZnO-Bi_2O_3$-catalyst, whereas a $ZnO-Na_2CO_3$-catalyst results in a somewhat lower conversion ratio of 70 to 90%.

The decomposition of the catalyst as a consequence of the peeling of the oxides from the metal shavings and a certain amount of continuous poisoning are the main problems involved in using these catalysts. U.S. Pat. No. 2,436,970 mentions a catalyst with brass as a carrier that had to be replaced after having worked for 80 days and nights at $F/W = 1\ h^{-1}$, the working temperature $T = 400°$ C. and $\alpha = 80\%$.

The activity of the catalyst is, of course, of great importance since it determines the amount of reactant, which is convertible per unit of time by means of a predetermined amount of catalytic material, but the selectivity of the catalyst is of even greater importance. The selectivity can be expressed as the portion of reactant used for the conversion, which is converted into the desired product. When dehydrogenating alcohols a number of undesired side reactions may occur when the selectivity of the catalyst is low. In the first place the alcohol may dehydrate during formation of an unsaturated hydrogen carbon, and furthermore the carbonyl compound formed by the dehydrogenation may condense when liberating water, whereby saturated or unsaturated compounds of higher molecular weight are formed.

Both dehydration and the so-called aldol condensation cause loss of product. Furthermore these side reactions involve large expense for removing the water formed from the carbonyl compound, since a water content above 1-2% is rarely tolerated during the use of the product, e.g. as a solvent. By using the above known catalysts for dehydrogenating 2-butanol into 2-butanon the selectivity is usually estimated to be 90-95% at a working temperature of 400° C., whereas the catalyst of the invention provides a selectivity of 98-99%, cf. the following Tables 2 to 7.

When selecting the carrier for the liquid catalytic metal several circumstances are to be considered. In the first place the fired carrier material must have a large pore volume and an appropriately small or narrow pore width in order to maintain the fused metal, and so that a large contact area between the reactant and the catalyst and easy passage of the reactant into the interior of the carrier are ensured. Subsequently, the carrier may not to any appreciable extent catalyze undesired side reactions.

Among oxides tabulated according to increasing acidity, CaO, MgO, ZnO, FeO, $Fe_2O_3$, $Cr_2O_3$, $TiO_2$, $Al_2O_3$, $SiO_2$, $WO_3$, it is well-known that the most basic oxides, CaO, MgO and ZnO result in the least dehydration when dehydrogenating alcohols. As previously mentioned, MgO and ZnO are commercially available and can be used in themselves as dehydrogenating catalysts, although their own activity is far less than the catalytic activity of liquid indium dispersed in the pore structure of these materials, cf. the following Table 1. On the contrary $Al_2O_3$ and $SiO_2$ cause considerable dehydration, for which reason they are less suitable as carriers. However, by forming Mg or Zn spinel ($MgAl_2O_4$ or $ZnAl_2O_4$), the basic and acidic properties of the carrier material can be neutralized and a carrier obtained, which in the respect of mechanical strength is somewhat better than a fired MgO-carrier, cf. the following Example 7. However, the selectivity of the spinel carrier is not nearly as good as the selectivity of the MgO carrier, and a MgO-carrier is therefore preferred in order not to reduce the selectivity of the catalyst in general.

In an embodiment of the process of the invention, $In_2O_3$ is mixed with MgO, whereby powdered $In_2O_3$ is mixed with powdered MgO containing 1 to 5% lubricant, preferably Mg-stearate, and compressed, preferably into pills or pearls, before the firing is performed.

Alternatively, $In_2O_3$ may be mixed with $Mg(OH)_2$, whereby powdered $In_2O_3$ is mixed with an aqueous $Mg(OH)_2$-gel during grinding to form a paste containing $In_2O_3$-granules under $5\mu$ in size uniformly dispersed in the $Mg(OH)_2$ vehicle, whereafter the paste is dried at 100°-150° C. for obtaining a dry matter content of 40-60% and extruded before the firing is performed.

A high firing temperature improves the mechanical strength of the carrier material, but simultaneously reduces its pore volume and interior surface. The best result is obtained when a catalyst based on MgO is fired at a temperature of just under 1000° C. for 5 to 20 hours. In comparison, a $MgOAl_2O_3$-carrier having the stoichiometric relations between MgO and $Al_2O_3$ necessary to form a spinel, must be fired at more than 1300° C. to ensure formation of the spinel structure, cf. Example 7. Firing the $MgO-In_2O_3$ catalyst at 950° C. followed by a second firing at 1040° C. results in a reduction of the activity and at the same time a slightly increasing selectivity compared to the catalyst only fired at 950° C., cf. the following Example 4. This is obviously due to a vitrification of the MgO structure at the higher temperature, whereby the In surface is closed to some extent and the influence of the less selective MgO is reduced.

Finally, the significance of the In-content of the catalyst should be mentioned. The following Tables 2 to 6 illustrate that the activity of a MgO-In catalyst passes a maximum at 0.5-1.5% In, said phenomenon being ascribed to the volume contraction and the reduction of the interior surface, cf. Example 4, which is noted at the firing of $In_2O_3$-MgO, and which probably is due to a partial spinel formation to $MgIn_2O_4$.

Just as the selection of carrier is important for the applicability of the catalyst, the selection of the catalytic material is, of course, also of great importance. The previously mentioned Japanese publications underline zinc as being the most active of the three fused metals Zn, In and Ga, and since it furthermore is the least expensive, it would be natural to produce the catalyst on the basis of this metal. However, zinc has two drawbacks, cf. the following Example 10. It is far easier to reduce $In_2O_3$ to In than ZnO to Zn, and zinc is far more volatile than indium. At 419° C., i.e. the melting point of zinc, the vapor pressure of indium is thus more than $10^{-10}$ mm Hg, whereas the vapor pressure of zinc is almost $10^{-1}$ mmHg. At 450° C. the vapor pressure of zinc is almost 1 mm Hg, for which reason zinc evaporates more quickly from a catalyst at this temperature, whereas indium only has a vapor pressure of about $10^{-9}$ mm Hg at 450° C. The analysis method for indium described below has never disclosed any loss of indium, not even during long-lasting dehydrogenation tests, cf. Example 6. When activating the catalyst in situ a gray coloring of the catalytic curve can be noted, said coloring resulting from volatile In-oxides (InO and $In_2O$) formed as intermediates during the reduction of $In_2O_3$ to In. Should these small losses of In increase too greatly, the catalyst can be separately activated, whereby 5 to 10 times the stoichiometric amount $H_2$ is passed across the fired catalyst pills at 400° C. during the collecting of the yellow to yellowish gray volatile $In_2O$ and InO vapors condensed in the cold portion of the activating reactor.

The test set-ups used and the analysis method for In are briefly described below to explain the runs mentioned in the Examples.

In Examples 2 to 7 a recirculation reactor is used. A constant feed flow of 2-butanol is passed by means of a dosage pump into an evaporator, wherein the 2-butanol is evaporated at 210° C. Through purifiers for oxygen, nitrogen can be mixed in the butanol flow and thereby act as a neutral diluent material, but the runs described in the Examples have been carried out without this addition of inert gases. Subsequently, the gas is passed into the reactor loop comprising the reactor and an outer recirculation loop. A bellow pump yielding 28 l gas/min. ensures that the recirculation ratio is very high (at a feeding of 37 grams butanol per hour the theoretic recirculation ratio is 98.3% at 400° C.), and the measured conversion ratio $\alpha$ may be correlated with the kinetics of the reaction r through the following expressions for an ideally stirred tank reactor with pure reactant in the feed flow:

$$F\alpha = r \cdot W,$$

wherein F may mean kilograms per hour, W may mean kilograms of catalyst and $\alpha$ is the conversion ratio ranging from 0 to 1.

A reaction of the type R-CHOH-R'→R-CO-R'+$H_2$ is obtained with, for instance, a kinetics of the first order $(r=k'(1-\alpha) \cdot c_o)$ $$\frac{F\alpha}{W} = k' \cdot \frac{1-\alpha}{1+\alpha} c_o \approx k(1-\alpha)$$

wherein $k'$ is the velocity constant ($k=k' \cdot c_o$), and $c_o$ is the alcohol concentration of the feed mixture. The factor $1+\alpha$ in the denominator, which is due to the volume increase at the reaction, is thus almost 2 when $\alpha \sim 1$. This means that a proportionality is almost obtained between $F\alpha/W$ and $(1-\alpha)$, provided the reaction temperature is selected in such a manner that the backward reaction is insignificant. During the runs performed with 2-butanol, the reaction is more than 98% displaced towards the formation of ketone provided the temperature is above 325° C., and the backward reaction can therefore be disregarded. In the Tables 1 to 6 the velocity constant of the first order is k ($h^{-1}$) calculated as $$\frac{F\alpha}{W(1-\alpha)}$$

and subsequently the capacity of an equivalent integral reactor for obtaining the recirculation reactor result is calculated as $$S = \frac{F}{W} \alpha = -\frac{k \cdot \alpha}{\ln(1-\alpha)}$$

for various values of $\alpha$.

This calculation, which is, of course, not based on any absolute knowledge of whether the reaction follows a simple kinetics of first order, only serves to provide a basis for comparison between results obtained with the catalyst of the invention and results obtained with the previously mentioned known catalysts.

The measuring of the conversion ratio $\alpha$ is performed by means of gas phase chromatography, whereby a sample is automatically taken in a test loop every 20 minutes. Areas corresponding to ketone, alcohol and side products are automatically calculated and transferred to a punched paper tape, from where they can later be further examined and transferred into a final form as illustrated in the Tables 1 to 7, showing the calculation results for the activity (S and k) and the selectivity.

The entire set-up is carefully supervised so that the reactor temperature and flow velocities are regulated within narrow limits. A programmed temperature cycle of 100° C. in steps of 15° C. may be run through during 24 hours in order to obtain acidity measurements as a function of the temperature.

Some tests, cf. Examples 8 to 10, are performed in an integral reactor inserted in the reactor system instead of the recirculation loop. Tests undertaken with this reactor were used for qualitative estimation of the comparative suitability of various catalyst preparations.

The analysis of the catalyst for In was performed before and after use in the reactor. 0.2 to 0.3 grams of catalyst material were boiled with a mixture of equal portions of concentrated nitric acid and water for 3 to 4 hours. The boiled mixture was diluted with water to 1 liter, of which 25 ml were diluted into 1000 ml with water, and from this weak In-solution buffered into pH=5.5, $In^{+3}$ was extracted with dithizone (6.5 mg in 500 ml $CCl_4$). The absorbance of the raspberry red In-dithizone complex is determined and compared to a standard curve.

When In is present in oxide form, the oxide is reduced with $H_2$ at 420° C. before boiling with acid.

Only the main result of the use of the catalyst illustrated in the Example is mentioned with reference to the Tables. Whereas the pure MgO-carrier has an activity comparable to the activity of commercially used catalysts, addition of only 0.1% In results in almost double the activity at lower temperatures (e.g. 323.5° C.). At higher temperatures (e.g. 420° C.) the difference in activity is insignificant, since the activation energy for the reaction with the carrier as catalyst is apparently larger than for the reaction with In as catalyst, for which reason an increase of the temperature favors the former reaction more than the latter. As low a reaction temperature as possible is preferred since the side reactions are favored by higher temperatures.

However, already with an In-content of 0.4%, the activity for the In-containing catalyst is many times larger than the activity for the carrier alone at all test temperatures.

The selectivities shown in Table 7 are all about 99%, which agrees very well with the results stated in the previously mentioned Japanese publications, which were obtained with pure, fused metals. Thus the carrier does not influence the selectivity.

Finally in connection with the long-lasting run in Example 6, it should be mentioned that the alcohol becomes somewhat homogeneously decomposed in the gas phase simultaneously with the In-catalyzed reaction, said alcohol decomposition probably being catalyzed by the reactor wall. Reaction products, e.g. carbon, are collected in the catalyst layer serving as a filter. An inspection of the catalyst after 50 days and nights shows smudging of the outer surface of the catalyst, in particular adjacent to the inlet for the gas mixture to the catalyst layer. The gradual loss of activity during the long-lasting test can probably be ascribed to this phenomenon, which is far less marked when using the catalyst in the normal manner, i.e. in an integral reactor, wherein the presence of the gas in the hot zone is very short.

The invention is illustrated but not limited by the following Examples.

EXAMPLE 1

Analytically pure MgO with 5% Mg-stearate as a binding agent is pelletized at 4 different pressures. Each sample is fired at two different temperatures, 950° C. and 1040° C. for 20 hours. The pellets have a diameter of 6 mm and a weight per mm height of the pills of 0.0436, 0.0410, 0.0347 and 0.0334 grams per mm respectively. The weight of the sample pelletized at the highest pressure is the greatest.

The weight loss is 17%, both when fired at 950° C. and at 1040° C. The high weight loss is due to the fact that besides stearate, hydroscopically combined water also evaporates from MgO. The pill diameter is insignificantly changed and amounts to 96-98% of the thickness measured before the firing.

After firing at 950° C., a slightly decreasing BET-area caused by increasing pelletizing pressure is obtained, ranging from 6.5 $m^2/g$ at the lowest pelletizing pressure to 5.8 $m^2/g$ at the highest pressure.

When fired at 1040° C. all the samples have the same BET-area of 5.5 $m^2/g$. Differences in the structure of the pills caused by varying pelletizing pressures are thus balanced at the higher firing temperature, at which a certain vitrification apparently takes place.

EXAMPLE 2

A second MgO-sample comprising 5% Mg-stearate is pelletized and fired for 20 hours at 950° C. The firing loss is 19.9%. Neither the pill diameter nor the pill thickness are changed during the firing.

The activity of this catalyst sample is determined in the recirculation reactor at F=40 grams 2-butanol per hour and at five temperatures varying from 468.5° C. to 330° C. The results of the activity (k) and the selectivity (S) are illustrated in Table 1.

EXAMPLE 3

A new sample of 34.1 grams of the carrier described in Example 2 was tested at a constant temperature of 405.5° C. and F=40.2 g/h. The activity was constant during the 16 hour test and equal to the activity stated in Table 1.

EXAMPLE 4

By means of careful grinding and mixing in a mortar, $In_2O_3$ was added to a carrier material with the same composition as the carrier material described in Examples 1 to 3 in an amount corresponding to a content of 3% In in the fired catalyst. The sample was pelletized, and the pellets were weighed and measured, after which they were fired at 950° C. for 20 hours. The weight loss was 20.2%, i.e. almost corresponding to the weight loss in the Examples 1 and 2. The pellet height was, however, reduced from 2.95 mm to 2.73 mm, whereas the pellet diameter was reduced from 6 mm to 5.6 mm, i.e. considerable shrinking occurred.

EXAMPLE 5

Pellets containing from 0.1% to 7.3% In were prepared as in Example 4 and used as a catalyst in the recirculation reactor.

Results obtained with various values of F, W and T appear from Tables 2 to 6. The selectivity appears from Table 7.

A partial sample was removed from the sample containing 0.1% In (Run 62 in Table 2). After firing at 950° C. for 20 hours this partial sample was subjected to a second firing at 1040° C. for an additional 20 hours. The activity of this sample (Run 62a) is compared in Table 2a to the sample fired only once at 950° C. The second firing at the higher temperature causes a certain drop in activity (vitrification) and a very slowly increasing selectivity from 98.9% at all three temperatures during Run 62, to 99.0% during Run 62a.

The hardness and the strength of said catalyst are obviously a function of the In-content. Thus, a pure MgO carrier fired at 950° C. can be crumbled manually, whereas a sample containing only 1% $In_2O_3$ is durable, also when subjected to slight impacts and blows. The shrinking and the increase in hardness are ascribed to a partial formation of $MgIn_2O_4$.

EXAMPLE 6

33.8 grams MgO containing 1.5% In was pelletized and fired at 950° C. and subsequently treated with 38 grams 2-butanol per hour in the recirculation reactor at the reaction temperature 400° C. for 50 days and nights.

During the first 10 days and nights the activity was constant, and a k-value of 33.81 $h^{-1}$ was estimated in accordance with the above formulas. This value agrees very well with results obtained by interpolation between the values stated in Table 41a.

Subsequently, a sudden drop (in the course of 20 minutes) in the conversion ratio $\alpha$ occurred from 96.7% to 95.5%, probably as a consequence of a working interruption in the gas chromatograph. During the succeeding 40 days and nights the activity decreased slowly, initially to $\alpha = 94\%$ after 23 days and nights, and subsequently to $\alpha = 92\%$ after 50 days and nights.

An inspection of the pellets after removal from the reactor showed that they were somewhat blackened with soot, particularly adjacent to the entrance to the curved path of the reactor. No loss of In occurred.

EXAMPLE 7

To a commercial $MgO-Al_2O_3$ powder of the molar ratio 1:1 $In_2O_3$ was added in order to obtain 7.3% In, and firing was performed for 18 hours, 4 hours of these at 1450° C. Table 8 illustrates how the conversion ratio $\alpha$ at 420° C. and the feed flow F=25.3 grams 2-butanol per hour are considerably smaller than is the case for the catalyst based on MgO, and furthermore that the selectivity is considerably smaller. After about 30 hours the drop in conversion ratio seems to cease and $\alpha$ may even increase a little. The further reacted amount of alcohol is, however, mainly converted into butene.

EXAMPLE 8

A quartz glass carrier having an almost uniform pore width of 306.0 nm was impregnated with an $In(NO_3)_3$-solution. The sample was initially dried at 80° C. for 4 hours and subsequently at 180° C. for an additional 4 hours. A sample of 5.3 grams contained 17% In. The activity of this sample was determined in an integral reactor at 420° C. and an alcohol dosage of F=40 grams per hour.

By measuring the conversion ratio every 5 minutes, a heavy drop in the conversion ratio was observed from almost 100% at the beginning of the test to 30% after 35 minutes. Subsequently, the activity dropped much more slowly, and after 3 days and nights the conversion ratio had dropped to 14%.

A microscopical examination of the glass particles (FIG. 2) showed that In had collected in large drops on the surface of the carrier. Some of the drops had fallen off and were present within the reactor.

EXAMPLE 9

0.727 grams $In_2O_3$ were stirred into aqueous $Mg(OH)_2$ during gelation thereof. The gel formed was dried to obtain a paste weighing 36.5 grams, and the paste was extruded and dried at 130° C. for 4 hours. Subsequently, the extruded matter was fired at 1000° C. for 18 hours.

With 3.98 grams of this sample and F=24 g/h the conversion ratio $\alpha$ was measured at 420° C. within the integral reactor. $\alpha$ was determined at 94%. After 2 hours, the feed flow F was raised to 40 grams per hour, and $\alpha$ was measured at 80%.

EXAMPLE 10

While stirring, 26.3 grams ZnO powder was added to 248 grams water glass together with 1½ liters water. Subsequently, a gelation at 5° C. was performed by adding 245 ml 4 N hydrochloric acid. The gel was washed, dried at 100° C. for an hour and then at 300° C. for 4 hours, whereafter it was reduced by $H_2$, initially at 400° C. for 4 hours and then at 600° C. for 4 hours.

Only a very slight reduction of ZnO to Zn at 400° C. occurred, whereas some reduction at 600° C. probably occurred, but Zn mainly left by evaporation and adhered to the cold portion of the reactor tube. By means of this test it was observed that ZnO is unfit as a starting carrier material for preparing a catalyst containing liquid, dispersed Zn as an active catalytic material.

The above gelation procedure was repeated with Zn powder instead of ZnO powder. The calcined catalyst was tested in the integral reactor (2.3 grams catalyst and 120 grams 2-butanol per hour), and a conversion ratio $\alpha = 35\%$ at 440° C. was obtained. The catalyst pellets were colored grayish black after 2 hours as a consequence of the carbon deposit on the SiO$_2$-carrier.

TABLE 1

Magnesium oxide without In, Run 57

| Catalyst in Grams | Temp. °C. | Feed Flow (g/h) | The conversion ratio $\alpha =$ k h$^{-1}$ | 0.80 S h$^{-1}$ | 0.90 S h$^{-1}$ | 0.95 S h$^{-1}$ | 0.97 S h$^{-1}$ | 0.98 S h$^{-1}$ |
|---|---|---|---|---|---|---|---|---|
| 34.28 | 468.50 | 40.0 | 13.42 | 6.67 | 5.24 | 4.26 | 3.71 | 3.36 |
| 34.28 | 405.50 | 40.0 | 1.68 | 0.83 | 0.66 | 0.53 | 0.46 | 0.42 |
| 34.28 | 405.50 | 40.2 | 0.96 | 0.48 | 0.38 | 0.30 | 0.27 | 0.24 |
| 34.28 | 405.50 | 40.2 | 1.52 | 0.75 | 0.59 | 0.48 | 0.42 | 0.38 |
| 34.28 | 375.00 | 40.00 | 0.92 | 0.46 | 0.36 | 0.29 | 0.25 | 0.23 |
| 34.28 | 358.00 | 40.0 | 0.61 | 0.30 | 0.24 | 0.19 | 0.17 | 0.15 |
| 34.28 | 330.0 | 40.0 | 0.26 | 0.13 | 0.10 | 0.08 | 0.07 | 0.06 |
| Temperature in °C. | | | 468.5 | 405.5 | | 375.0 | | 330.0 |
| Selectivity in % at alcohol feed flow 40 g/h | | | 97.8 | 97.0 | | 97.5 | | 97.9 |

TABLE 2

Magnesium oxide + 0.1% In, Run 62

| Catalyst in Grams | Temp. °C. | Feed Flow (g/h) | The conversion ratio $\alpha =$ k h$^{-1}$ | 0.80 S h$^{-1}$ | 0.90 S h$^{-1}$ | 0.95 S h$^{-1}$ | 0.97 S h$^{-1}$ | 0.98 S h$^{-1}$ |
|---|---|---|---|---|---|---|---|---|
| 32.29 | 420.00 | 25.2 | 13.94 | 6.93 | 5.45 | 4.42 | 3.86 | 3.49 |
| 32.29 | 405.00 | 25.2 | 10.56 | 5.25 | 4.13 | 3.35 | 2.92 | 2.65 |
| 32.29 | 389.50 | 25.2 | 6.01 | 2.99 | 2.35 | 1.90 | 1.66 | 1.50 |
| 32.29 | 372.50 | 25.2 | 2.74 | 1.36 | 1.07 | 0.87 | 0.76 | 0.69 |
| 32.29 | 355.00 | 25.2 | 1.45 | 0.72 | 0.57 | 0.46 | 0.40 | 0.36 |
| 32.29 | 335.00 | 25.2 | 0.75 | 0.37 | 0.29 | 0.24 | 0.21 | 0.19 |
| 32.29 | 323.50 | 25.2 | 0.49 | 0.24 | 0.19 | 0.15 | 0.13 | 0.12 |
| 32.29 | 420.0 | 52.7 | 17.57 | 8.73 | 6.87 | 5.57 | 4.86 | 4.40 |
| 32.29 | 405.50 | 52.7 | 12.94 | 6.43 | 5.06 | 4.10 | 3.58 | 3.24 |
| 32.29 | 389.50 | 52.7 | 7.69 | 3.82 | 3.01 | 2.44 | 2.13 | 1.93 |
| 32.29 | 372.50 | 52.7 | 4.41 | 2.19 | 1.72 | 1.40 | 1.22 | 1.11 |
| 32.29 | 355.00 | 52.7 | 2.45 | 1.22 | 0.96 | 0.78 | 0.68 | 0.61 |
| 32.29 | 355.00 | 52.7 | 1.48 | 0.74 | 0.58 | 0.47 | 0.41 | 0.37 |
| 32.20 | 323.50 | 52.7 | 0.92 | 0.46 | 0.36 | 0.29 | 0.25 | 0.23 |

TABLE 2a:

Firing at 950° C. (Run 62) succeeded by firing at 1040° C. (Run 62a). The Conversion ratio $\alpha$ in %

| | Temp.°C. | 405 | 389 | 372 |
|---|---|---|---|---|
| $\alpha$ | (Run 62) | 92 | 88 | 76 |
| $\alpha$ | (Run 62a) | 89 | 83 | 72 |

TABLE 3

Magnesium oxide + 0.4% In, Run 61

| Catalyst in Grams | Temp.°C. | Feed Flow (g/h) | The conversion ratio $\alpha =$ k h$^{-1}$ | 0.80 S h$^{-1}$ | 0.90 S h$^{-1}$ | 0.95 S h$^{-1}$ | 0.97 S h$^{-1}$ | 0.98 S h$^{-1}$ |
|---|---|---|---|---|---|---|---|---|
| 34.18 | 420.50 | 24.9 | 49.96 | 24.83 | 19.63 | 15.84 | 13.82 | 12.52 |
| 34.18 | 405.00 | 24.9 | 34.03 | 16.92 | 13.30 | 10.79 | 9.41 | 8.52 |
| 34.18 | 389.50 | 24.3 | 20.46 | 10.17 | 8.00 | 6.49 | 5.66 | 5.12 |
| 34.18 | 372.50 | 24.3 | 10.07 | 5.00 | 3.93 | 3.19 | 2.78 | 2.52 |
| 34.18 | 355.00 | 24.3 | 4.44 | 2.21 | 1.74 | 1.41 | 1.23 | 1.11 |
| 34.18 | 335.50 | 24.3 | 2.13 | 1.06 | 0.83 | 0.68 | 0.59 | 0.53 |
| 34.18 | 323.50 | 24.9 | 1.10 | 0.55 | 0.43 | 0.35 | 0.31 | 0.28 |
| 34.17 | 420.00 | 38.8 | 58.63 | 29.14 | 22.92 | 18.59 | 16.22 | 14.69 |
| 34.17 | 405.50 | 38.8 | 40.92 | 20.34 | 15.99 | 12.98 | 11.32 | 10.25 |
| 34.17 | 389.50 | 38.8 | 25.27 | 12.56 | 9.88 | 8.01 | 6.99 | 6.33 |
| 34.17 | 372.50 | 38.8 | 11.92 | 5.92 | 4.66 | 3.78 | 3.30 | 2.99 |
| 34.17 | 355.00 | 38.8 | 5.35 | 2.66 | 2.09 | 1.70 | 1.48 | 1.34 |
| 34.17 | 335.50 | 38.8 | 2.65 | 1.32 | 1.04 | 0.84 | 0.73 | 0.66 |
| 34.17 | 323.50 | 38.8 | 1.51 | 0.75 | 0.59 | 0.48 | 0.42 | 0.38 |
| 34.18 | 420.00 | 94.5 | 74.03 | 36.80 | 28.94 | 23.48 | 20.48 | 18.55 |
| 34.18 | 405.50 | 94.5 | 53.66 | 26.67 | 20.97 | 17.02 | 14.84 | 13.44 |
| 34.18 | 389.50 | 94.5 | 33.61 | 16.71 | 13.14 | 10.66 | 9.30 | 8.42 |
| 34.18 | 372.50 | 94.5 | 19.01 | 9.45 | 7.43 | 6.03 | 5.26 | 4.76 |
| 34.18 | 355.00 | 94.5 | 10.40 | 5.17 | 4.07 | 3.30 | 2.88 | 2.61 |
| 34.18 | 335.50 | 94.5 | 6.15 | 3.06 | 2.41 | 1.95 | 1.70 | 1.54 |

TABLE 3-continued

Magnesium oxide + 0.4% In, Run 61

| Catalyst in Grams | Temp.°C. | Feed Flow (g/h) | The conversion ratio α = | 0.80 | 0.90 | 0.95 | 0.97 | 0.98 |
|---|---|---|---|---|---|---|---|---|
| | | | k h$^{-1}$ | S h$^{-1}$ | S h$^{-1}$ | S h$^{-1}$ | S h$^{-1}$ | S h$^{-1}$ |
| 34.18 | 323.50 | 94.5 | 4.15 | 2.06 | 1.62 | 1.32 | 1.15 | 1.04 |

TABLE 4a

Magnesium oxide + 1.5% In, Run 60

| Catalyst in Grams | Temp.°C. | Feed Flow (g/h) | The conversion ratio α = | 0.80 | 0.90 | 0.95 | 0.97 | 0.98 |
|---|---|---|---|---|---|---|---|---|
| | | | k h$^{-1}$ | S h$^{-1}$ | S h$^{-1}$ | S h$^{-1}$ | S h$^{-1}$ | S h$^{-1}$ |
| 34.33 | 420.00 | 40.00 | 64.29 | 31.96 | 25.13 | 20.39 | 17.79 | 16.11 |
| 34.33 | 405.00 | 40.00 | 37.67 | 18.73 | 14.73 | 11.95 | 10.42 | 9.44 |
| 34.33 | 389.50 | 40.00 | 22.14 | 11.00 | 8.65 | 7.02 | 6.12 | 5.55 |
| 34.33 | 372.50 | 40.0 | 9.24 | 4.59 | 3.61 | 2.93 | 2.56 | 2.31 |
| 34.33 | 355.00 | 40.0 | 5.57 | 2.77 | 2.18 | 1.77 | 1.54 | 1.40 |
| 34.33 | 335.50 | 40.0 | 3.35 | 1.67 | 1.31 | 1.06 | 0.93 | 0.84 |
| 34.33 | 323.50 | 40.0 | 2.37 | 1.18 | 0.92 | 0.75 | 0.65 | 0.59 |

TABLE 4b

Magnesium oxide + 1.5% In, Run 50

| Catalyst in Grams | Temp.°C. | Feed Flow (g/h) | The conversion ratio α = | 0.80 | 0.90 | 0.95 | 0.97 | 0.98 |
|---|---|---|---|---|---|---|---|---|
| | | | k h$^{-1}$ | S h$^{-1}$ | S h$^{-1}$ | S h$^{-1}$ | S h$^{-1}$ | S h$^{-1}$ |
| 34.34 | 420.00 | 95.3 | 70.26 | 34.92 | 27.46 | 22.28 | 19.43 | 17.60 |
| 34.34 | 405.00 | 95.3 | 39.27 | 19.52 | 15.35 | 12.45 | 10.86 | 9.84 |
| 34.34 | 355.00 | 95.3 | 8.55 | 4.52 | 3.34 | 2.71 | 2.37 | 2.14 |
| 34.34 | 335.50 | 95.3 | 4.93 | 2.45 | 1.93 | 1.56 | 1.36 | 1.24 |
| 34.34 | 323.00 | 95.3 | 3.01 | 1.49 | 1.18 | 0.95 | 0.83 | 0.75 |
| 34.34 | 389.50 | 40.0 | 19.27 | 9.48 | 7.53 | 6.11 | 5.33 | 4.83 |
| 34.34 | 372.50 | 40.0 | 9.42 | 4.68 | 3.68 | 2.99 | 2.61 | 2.36 |

TABLE 5

Magnesium oxide + 3.0% In, Run 56

| Catalyst in Grams | Temp.°C. | Feed Flow (g/h) | The conversion ratio α = | 0.80 | 0.90 | 0.95 | 0.97 | 0.98 |
|---|---|---|---|---|---|---|---|---|
| | | | k h$^{-1}$ | S h$^{-1}$ | S h$^{-1}$ | S h$^{-1}$ | S h$^{-1}$ | S h$^{-1}$ |
| 34.32 | 420.00 | 25.4 | 45.43 | 22.58 | 17.76 | 14.41 | 12.57 | 11.38 |
| 34.32 | 405.00 | 25.4 | 23.88 | 11.87 | 9.33 | 7.57 | 6.61 | 5.98 |
| 34.32 | 389.50 | 25.4 | 10.99 | 5.46 | 4.29 | 3.48 | 3.04 | 2.75 |
| 34.32 | 372.50 | 25.4 | 5.68 | 2.83 | 2.22 | 1.80 | 1.57 | 1.42 |
| 34.32 | 355.00 | 25.4 | 3.23 | 1.61 | 1.26 | 1.03 | 0.89 | 0.81 |
| 34.32 | 335.50 | 25.4 | 1.81 | 0.90 | 0.71 | 0.57 | 0.50 | 0.45 |
| 34.32 | 323.50 | 25.4 | 1.22 | 0.61 | 0.48 | 0.39 | 0.34 | 0.31 |
| 34.32 | 420.00 | 40.4 | 47.87 | 23.80 | 18.71 | 15.18 | 13.24 | 11.99 |
| 34.32 | 405.00 | 40.4 | 21.46 | 10.67 | 8.39 | 6.81 | 5.94 | 5.38 |
| 34.32 | 389.50 | 40.4 | 11.76 | 5.84 | 4.60 | 3.73 | 3.25 | 2.95 |
| 34.32 | 372.50 | 53.6 | 8.20 | 4.08 | 3.20 | 2.60 | 2.27 | 2.05 |
| 34.32 | 355.00 | 53.6 | 5.44 | 2.70 | 2.13 | 1.73 | 1.51 | 1.36 |
| 34.32 | 335.50 | 53.6 | 3.24 | 1.61 | 1.27 | 1.03 | 0.90 | 0.81 |
| 34.32 | 323.50 | 53.6 | 2.27 | 1.13 | 0.89 | 0.72 | 0.63 | 0.57 |
| 34.32 | 420.00 | 87.5 | 52.89 | 26.29 | 20.67 | 16.77 | 14.63 | 13.25 |
| 34.32 | 405.00 | 87.5 | 27.81 | 13.82 | 10.87 | 8.82 | 7.69 | 6.97 |
| 34.32 | 389.00 | 87.5 | 17.07 | 8.48 | 6.67 | 5.41 | 4.72 | 4.28 |
| 34.32 | 372.50 | 87.3 | 11.13 | 5.53 | 4.35 | 3.53 | 3.08 | 2.79 |
| 34.32 | 355.00 | 87.3 | 7.27 | 3.62 | 2.84 | 2.31 | 2.01 | 1.82 |
| 34.32 | 335.50 | 87.3 | 4.40 | 2.19 | 1.72 | 1.40 | 1.22 | 1.10 |
| 34.32 | 323.50 | 87.3 | 3.11 | 1.54 | 1.21 | 0.99 | 0.86 | 0.78 |

TABLE 6

Magnesium oxide + 7.3% In, Run 53

| Catalyst in Grams | Temp.°C. | Feed Flow (g/h) | The conversion ratio α = | 0.80 | 0.90 | 0.95 | 0.97 | 0.98 |
|---|---|---|---|---|---|---|---|---|
| | | | k h$^{-1}$ | S h$^{-1}$ | S h$^{-1}$ | S h$^{-1}$ | S h$^{-1}$ | S h$^{-1}$ |
| 34.25 | 420.00 | 25.5 | 35.45 | 17.62 | 13.86 | 11.24 | 9.81 | 8.88 |
| 34.25 | 405.00 | 25.5 | 18.78 | 9.33 | 7.34 | 5.95 | 5.19 | 4.70 |
| 34.25 | 389.50 | 25.5 | 9.71 | 4.83 | 3.80 | 3.08 | 2.69 | 2.43 |

TABLE 6-continued

Magnesium oxide + 7.3% In, Run 53

| Catalyst in Grams | Temp.°C. | Feed Flow (g/h) | The conversion ratio α = | | | | |
|---|---|---|---|---|---|---|---|
| | | | 0.80 | 0.90 | 0.95 | 0.97 | 0.98 |
| | | | k h$^{-1}$ | S h$^{-1}$ | S h$^{-1}$ | S h$^{-1}$ | S h$^{-1}$ | S h$^{-1}$ |
| 34.25 | 372.50 | 25.5 | 5.49 | 2.73 | 2.15 | 1.74 | 1.52 | 1.38 |
| 34.25 | 355.00 | 25.5 | 3.28 | 1.63 | 1.28 | 1.04 | 0.91 | 0.82 |
| 34.25 | 335.50 | 25.5 | 1.82 | 0.90 | 0.71 | 0.58 | 0.50 | 0.45 |
| 34.25 | 323.00 | 25.5 | 1.19 | 0.59 | 0.47 | 0.38 | 0.33 | 0.30 |
| 34.21 | 420.00 | 41.8 | 38.45 | 19.11 | 15.03 | 12.19 | 10.64 | 9.63 |
| 34.21 | 405.00 | 41.8 | 21.07 | 10.48 | 8.24 | 6.68 | 5.83 | 5.28 |
| 34.21 | 389.50 | 41.8 | 11.57 | 5.75 | 4.52 | 3.67 | 3.20 | 2.90 |
| 34.21 | 372.50 | 41.8 | 7.14 | 3.55 | 2.79 | 2.26 | 1.97 | 1.79 |
| 34.21 | 355.00 | 41.8 | 4.51 | 2.24 | 1.76 | 1.43 | 1.25 | 1.13 |
| 34.21 | 335.50 | 41.8 | 2.68 | 1.33 | 1.05 | 0.85 | 0.74 | 0.67 |
| 34.21 | 323.00 | 41.8 | 1.76 | 0.87 | 0.69 | 0.56 | 0.49 | 0.44 |
| 34.25 | 420.00 | 120.4 | 33.64 | 16.72 | 13.15 | 10.67 | 9.31 | 8.43 |
| 34.25 | 405.00 | 120.4 | 22.45 | 11.16 | 8.77 | 7.12 | 6.21 | 5.62 |
| 34.25 | 389.50 | 120.4 | 16.05 | 7.98 | 6.27 | 5.09 | 4.44 | 4.02 |
| 34.25 | 372.50 | 120.4 | 11.10 | 5.52 | 4.34 | 3.52 | 3.07 | 2.78 |
| 34.25 | 355.00 | 120.4 | 7.55 | 3.75 | 2.95 | 2.40 | 2.09 | 1.89 |
| 34.25 | 335.00 | 120.4 | 4.60 | 2.29 | 1.80 | 1.46 | 1.27 | 1.15 |
| 34.25 | 323.50 | 120.4 | 2.57 | 1.28 | 1.01 | 0.82 | 0.71 | 0.65 |

TABLE 7

| | Selectivities (%) | | | | |
|---|---|---|---|---|---|
| In-content in % | 0.1 | 0.4 | 3.0 | 7.3 | |
| Alcohol feed flow g/h | 25.2 | 24.8 | 25.4 | 25.5 | |
| 420.0° C. | 98.8 | 98.8 | 98.3 | 98.5 | |
| 405.0° C. | 98.8 | 98.9 | 98.5 | 98.6 | |
| 372.5° C. | 98.9 | 98.7 | 98.5 | 98.8 | |
| 323.5° C. | 98.0 | 98.3 | 98.6 | 98.9 | |
| In-content in % | 0.1 | 0.4 | 1.5 | 3.0 | 7.3 |
| Alcohol feed flow g/h | 39.2 | 39.7 | 40.0 | 40.3 | 41.8 |
| 420.0° C. | 98.7 | 98.8 | 98.4 | 98.3 | 98.6 |
| 405.0° C. | 98.9 | 98.9 | 98.5 | 98.5 | 98.7 |
| 372.5° C. | 98.9 | 98.7 | 98.6 | 98.6 | 98.8 |
| 323.5° C. | 98.3 | 98.6 | 98.8 | — | 98.9 |
| In-content in % | 0.1 | 0.4 | 1.5 | 3.0 | 7.3 |
| Alcohol feed flow g/h | 52.4 | 94.2 | 95.3 | 87.3 | 120.0 |
| 420.0° C. | 98.9 | 99.0 | 98.7 | 98.6 | 98.9 |
| 405.0° C. | 99.0 | 99.0 | 98.8 | 98.7 | 98.9 |
| 372.5° C. | 99.0 | 98.8 | 98.8 | 98.8 | 98.9 |
| 323.5° C. | 98.5 | 98.8 | 98.9 | 98.9 | 99.0 |

TABLE 8:

7.3% In on spinel carrier fired at 1450° C.

| Time after beginning of the test (hours) | 3 | 5 | 10 | 20 | 30 | 40 |
|---|---|---|---|---|---|---|
| α (%) | 59 | 53 | 46 | 42 | 43 | 44 |
| Selectivity (%) | 95.8 | 95.4 | 94.8 | 93.7 | 93.1 | 92.5 |

We claim:

1. A catalyst for dehydrogenating an organic compound reactant in the gaseous phase comprising a solid state carrier material having a porosity of from about 0.2 to 0.7 cm$^3$/cm$^3$, and an active catalytic metal selected from the group consisting of indium and zinc within the pores of said carrier, said catalytic metal being in the liquid state at the reaction temperature of the gaseous reactant and forming droplets having diameters ranging from about 0.3 to 2.0 microns, said droplets being encased in pores forming cavities having diameters greater than the diameters of the respective droplets therein contained, said cavities being interconnected to other pores having diameters less than the diameters of the metal droplets and forming a system of interconnected ducts connecting the external surface of the carrier with the surfaces of the metal droplets, and said carrier material having a contact angle of more than 90° in contacting the liquid metal droplets.

2. A catalyst according to claim 1, wherein the carrier has a BET-surface area of from about 0.5 to 10 m$^2$/g.

3. A catalyst according to claim 1, wherein the active catalytic metal is indium, which is present in an amount of from about 0.05 to 10.0 g./100 g. of fired catalyst.

4. A catalyst according to claim 3, wherein the indium content is from about 0.5 to 1.5 g/100 g of fired catalyst.

5. A process for preparing a catalyst for dehydrogenating organic compounds comprising mixing a powdered source of an active catalytic metal selected from the group consisting of In$_2$O$_3$ and ZnO with a carrier material selected from the group consisting of oxides and hydroxides of Mg, Al, Si, Ca, Ti, Cr, Zn, W and mixtures thereof, firing the resulting mixture at a temperature of from about 900° to 1150° C. for about 5 to 20 hours, activating the catalyst by subjecting the same at a temperature of from about 320° to 440° C. to contact with a gas selected from the group consisting of reducing gases and an organic compound to be dehydrogenated, until 2 to 3 times the calculated stoichiometric amount of gas for complete reduction of In$_2$O$_3$ to In or ZnO to Zn respectively has passed through the catalyst.

6. A process according to claim 5, wherein powdered In$_2$O$_3$ is mixed with powdered MgO containing a lubricant, and the mixture is compressed into pellets before firing the same.

7. A process according to claim 5, wherein powdered In$_2$O$_3$ is mixed with an aqueous Mg(OH)$_2$ gel while grinding to form a paste containing In$_2$O$_3$ granules under 5u in size uniformly dispersed in the Mg(OH)$_2$ gel, drying the paste at about 100° to 150° C. to a dryness of from about 40 to 60% and extruding the so dried product before firing the same.

* * * * *